(12) United States Patent
Borchert et al.

(10) Patent No.: US 7,943,160 B2
(45) Date of Patent: May 17, 2011

(54) PEST CONTROL METHODS

(75) Inventors: Jeff N. Borchert, Fort Collins, CO (US); Richard M. Poché, Wellington, CO (US)

(73) Assignee: Scimetrics Limited Corp., Fort Collins, CO (US)

( * ) Notice: Subject to any disclaimer, the term of this patent is extended or adjusted under 35 U.S.C. 154(b) by 1169 days.

(21) Appl. No.: 11/260,034

(22) Filed: Oct. 25, 2005

(65) Prior Publication Data

US 2006/0057178 A1  Mar. 16, 2006

Related U.S. Application Data

(63) Continuation-in-part of application No. 10/430,708, filed on May 6, 2003, now abandoned.

(60) Provisional application No. 60/379,020, filed on May 9, 2002.

(51) Int. Cl.
*A01N 25/12* (2006.01)

(52) U.S. Cl. ........ 424/410; 424/405; 424/604; 514/341; 514/432; 514/453; 514/557; 514/681; 514/682

(58) Field of Classification Search .................. None
See application file for complete search history.

(56) References Cited

U.S. PATENT DOCUMENTS

| | | | |
|---|---|---|---|
| 4,169,719 A | 10/1979 | Levitt | |
| 4,237,113 A | 12/1980 | Cardarelli | |
| 4,394,506 A | 7/1983 | Levitt | |
| 4,663,346 A | 5/1987 | Coulston et al. | |
| 4,756,118 A | 7/1988 | Evans, II | |
| 5,198,467 A | 3/1993 | Milks | |
| 5,246,936 A | 9/1993 | Treacy et al. | |
| 5,413,784 A | 5/1995 | Wright et al. | |
| 5,609,879 A | 3/1997 | Myles | |
| 5,667,816 A | 9/1997 | Moss | |
| 5,733,935 A | 3/1998 | Andoh et al. | |
| 5,806,237 A * | 9/1998 | Nelson et al. | .................. 43/131 |
| 5,839,224 A | 11/1998 | Emerson et al. | |
| 5,866,514 A | 2/1999 | Sugisawa et al. | |
| 5,871,780 A | 2/1999 | Moss | |
| 5,928,634 A | 7/1999 | Uick et al. | |
| 6,156,309 A | 12/2000 | Miller et al. | |

(Continued)

FOREIGN PATENT DOCUMENTS

EP  0295117  4/2000

(Continued)

OTHER PUBLICATIONS

Bennington, E. 1960. A Systemic Insecticide and Diet composition for Flea and Rat Control. Journal of Economic Entomology 53(1): 169-170.

(Continued)

*Primary Examiner* — Neil Levy
(74) *Attorney, Agent, or Firm* — Swanson & Bratschun, L.L.C.

(57) ABSTRACT

Certain embodiments of the methods and compositions of matter disclosed herein relate to: "simultaneous" control of rodents and at least one insect pest (e.g., cockroach, ant, tick) using the same bait; control of ticks by orally administering to mammals a diet composition comprising fipronil; enhancing insecticide efficacy through use of a diet composition that comprises a Generation-I rodenticide and an insecticide; use of imidacloprid in a diet composition orally administerable to mammals in an uncontrolled setting; and use of at least one insecticide to enhance the efficacy of a rodenticide.

7 Claims, 2 Drawing Sheets

U.S. PATENT DOCUMENTS

| | | | |
|---|---|---|---|
| 6,248,730 | B1 * | 6/2001 | Poche .................. 514/154 |
| 6,369,078 | B1 | 4/2002 | Bowen et al. |
| 6,387,388 | B1 | 5/2002 | Misselbrook et al. |
| 6,468,523 | B1 | 10/2002 | Mettus et al. |
| 6,528,484 | B1 | 3/2003 | Ensign et al. |
| 6,552,076 | B2 | 4/2003 | Pei et al. |
| 6,750,256 | B1 | 6/2004 | Crandall, Jr. et al. |
| 6,849,633 | B2 * | 2/2005 | Okui et al. ............ 514/255.05 |
| 6,939,831 | B1 | 9/2005 | Caminade et al. |
| 2002/0002195 | A1 | 1/2002 | Huang et al. |
| 2002/0114821 | A1 | 8/2002 | Lescota et al. |
| 2002/0173543 | A1 | 11/2002 | Pei et al. |
| 2002/0187178 | A1 | 12/2002 | Roe |
| 2002/0193411 | A1 | 12/2002 | Huang et al. |
| 2003/0068335 | A1 | 4/2003 | Mettus et al. |
| 2003/0108585 | A1 | 6/2003 | Roe et al. |
| 2003/0124607 | A1 | 7/2003 | Stutzman-Engwall et al. |
| 2003/0143254 | A1 | 7/2003 | Dyker et al. |
| 2003/0143589 | A1 | 7/2003 | Baughn et al. |
| 2003/0203859 | A1 | 10/2003 | Bruce |
| 2003/0207806 | A1 | 11/2003 | Ensign et al. |
| 2003/0207869 | A1 | 11/2003 | Kraatz et al. |
| 2003/0215481 | A1 | 11/2003 | Borchert et al. |
| 2003/0232415 | A1 | 12/2003 | Stutzman-Engwall et al. |
| 2003/0235601 | A1 | 12/2003 | Hallahan |
| 2004/0009560 | A1 | 1/2004 | Stutzman-Engwall et al. |
| 2004/0014784 | A1 | 1/2004 | Jakobi et al. |
| 2004/0057977 | A1 | 3/2004 | Gardner et al. |
| 2004/0077713 | A1 | 4/2004 | Maupin et al. |
| 2004/0091894 | A1 | 5/2004 | Wisnewski et al. |
| 2004/0156920 | A1 | 8/2004 | Kane |
| 2004/0209896 | A1 | 10/2004 | Jeschke et al. |
| 2004/0209962 | A1 | 10/2004 | Crandall et al. |
| 2004/0253588 | A1 | 12/2004 | Baughn et al. |
| 2005/0069568 | A1 | 3/2005 | Hallahan |
| 2005/0070576 | A1 | 3/2005 | Spooner-Hart et al. |
| 2005/0112166 | A1 | 5/2005 | Hallahan |
| 2005/0137244 | A1 | 6/2005 | Boeckh et al. |
| 2005/0176818 | A1 | 8/2005 | Maupin et al. |
| 2005/0182059 | A1 | 8/2005 | Winzenberg et al. |
| 2005/0186147 | A1 | 8/2005 | Tamarkin et al. |
| 2005/0187289 | A1 | 8/2005 | Dolan et al. |
| 2005/0196777 | A1 | 9/2005 | McArthur et al. |
| 2005/0203149 | A1 * | 9/2005 | Kawata et al. ............ 514/357 |
| 2005/0234119 | A1 | 10/2005 | Soll et al. |

FOREIGN PATENT DOCUMENTS

| | | |
|---|---|---|
| WO | WO 00/62616 | 10/2000 |
| WO | WO 01/60409 | 8/2001 |

OTHER PUBLICATIONS

Clark, P.H., M.M. Cole. 1968. Systemic Insecticides for Control of Oriental Rat Fleas: Bait Tests with Hooded White Rats. Journal of Economic Entomology 61(2): 505-508.

Clark, P.H., M.M. Cole. 1971. Systemic Insecticides for Control of Oriental Rat Fleas: Preliminary Tests in Guinea Pigs, 1967-1969. Journal of Economic Entomology 64(6): 1477-1479.

Clark, P.H., M.M. Cole. 1974. Oriental Rat Fleas: Evaluation of Three Systemic Insecticides in Baits for Control on Cotton Rats in Outdoor Pens. Journal of Economic Entomology 67(2): 235-236.

Cole, M.M., W.C. Bennet, G.N. Graves, J.R. Wheeler, B.E. Miller and P.H. Clark. 1976. Dichlorvos Bait for Control of Fleas on Wild Rodents. Journal of Medical Entomology 12(6): 625-630.

Davis, R.M. 1999. Use of Orally Administered Chitin Inhibitor (Lufenuron) to Control Flea Vectors of Plague on Ground Squirrels in California. Journal of Medical Entomology 36(5): 562-567.

Harvey, T.L. 1960. Control of the Oriental Rat Flea with Systemic Insecticides Fed to Rats. Journal of Economic Entomology 53(1): 167-168.

Karhu, R., S. Anderson. 2000a. Effects of Pyriproxyfen Spray, Powder, and Oral Bait Treatments on the Relative Abundance of Fleas (Siphonaptera: Ceratophyllidae) in Black-Tailed Prairie Dog (Rodentia: Sciuridae) Towns. Journal of Medical Entomology 37(6): 864-871.

Larsen, K.S., H. Leirs, J. Lodal. 1998. Palatability and Toxicity Tests of Fipronil as a Systemic Insecticide in a Rodenticide Bait for Rat and Flea Control. Danish Pest Infestation Laboratory Annual Report, Item 13.3.4.

Larsen, K.S., J. Lodal. 1997. Evaluation of Systemic Insecticides Mixed in Rodenticide Diet compositions for Plague Vector Control. Belgium Journal of Zoology 127, Supplement 1: 119-127.

Leirs, H., K.S. Larsen, J. Lodal. 2001. Palatability and Toxicity of Fipronil as a Systemic Insecticide in a Bromadialone Rodenticide Diet composition for Rat and Flea Control. Medical and Veterinary Entomology 15: 299-303.

Lizzio, L.F. 1986. A boric acid-rodenticide mixture used in the control of coexisting rodent-cockroach infestations. Lab Anim Sci. Feb. 1986;36(1):74-6.

Miller, B.E., W.C. Bennet, G.N. Graves, J.R. Wheeler. 1975. Field Studies of Systemic Insecticides I. Evaluation of Phoxim for Control of Fleas on Cotton Rats. Journal of Medical Entomology 12(4): 425-430.

Miller, B.E., W.C. Bennet, G.N. Graves, J.R. Wheeler. 1977a. Field Studies of Systemic Insecticides II. Evaluation of Chlorphoxim for Control of Fleas on Five Rodent Species. Journal of Medical Entomology 14(2): 161-166.

Miller, B.E., J.W. Edwards, W.C. Bennet, G.N. Graves, J.R. Wheeler. 1977b. Field Studies of Systemic Insecticides III. Evaluation of Phoxim for Control of Fleas on Kangaroo Rats and Associated Species. Journal of Medical Entomology 14(3): 263-269.

Rand, P.W., E.H. Lacombe, M.S. Holman, C. Lubelczyk, R.P. Smith. 2000. Attempt to Control Ticks (Acari: Ixodidae) on Deer on a Isolated Island Using Ivermectin-Treated Corn. 37(1): 126-133.

Slowik, T.J., R.S. Lane, R.M. Davis. 2001. Field Trial of Systemically Delivered Arthropod Development-Inhibitor (Fluazuron) Used to Control Woodrat Fleas (Siphonaptera: Ceratophyllidae) and Ticks (Acari: Ixodidae). Journal of Medical Entomology 38(1): 75-84.

* cited by examiner

Fig.. 1

PEST CONTROL METHODS

This application is a continuation-in-part application of U.S. non-provisional application Ser. No. 10/430,708, filed May 6, 2003, published Nov. 20, 2003 with Pub. No. US 2003/0215481, said non-provisional application itself claiming priority to U.S. provisional application No. 60/379,020, filed May 9, 2002, said applications hereby incorporated herein by reference, said earlier-filed, parent non-provisional application pending during the filing of the instant application.

I. BACKGROUND OF THE INVENTION

At least one embodiment of the inventive technology relates to the control of pests. More particularly, certain embodiments may relate to the control of larvae, subadult and adult ticks on rodents with insecticides. Embodiments may also relate to the control of larvae, subadult and adult ticks or fleas on rodents with insecticides or insect growth regulators in combination with rodenticides (e.g., slow-acting rodenticides) for simultaneous control of ectoparasites and their mammalian hosts. Aspects of the inventive technology also relates to the simultaneous control of rodents and/or cockroaches and rodents and/or ants using insecticides and rodenticides in combinations.

Diet compositions formulated to target rodents are colloquially referred to as "bait" or "rodent bait". There are many commercially available "rodent baits"—containing poisons lethal to rodents—that are available to consumers and pest control professionals.

Diet compositions that are provided to wild rodents and mammals allow for the oral administration of chemicals including rodenticides, insecticides and/or insect growth regulators to insects, rodents or mammals. Insects, rodents or mammals consume the diet compositions, which contain rodenticides, insecticides and/or insect growth regulators. Oral administration of diet compositions to rodents or other mammals may involve simply placing the diet composition (a broad term that includes what is typically referred to as "bait") includes the simple act of setting out the composition (e.g., placing it in an area that may be trafficked by the mammal of interest) and the resultant consumption of the composition by an animal (e.g., a host mammal). Such consumption by a host mammal exposes not only the mammal to the ingredients of the composition (e.g., rodenticides, insecticides and/or insect growth regulators in the diet compositions), but also results in the exposure of the blood-feeding ectoparasites of these animals to these ingredients when they take a blood meal from that mammal.

Rodent diet compostions are formulated by many methods that are well known to individuals of ordinary skill in the art. As diet composition vehicles (which are types of inert ingredients, a term generally referring to ingredients that, unlike rodenticides and insecticides, are non-toxic), various grains could be used, including corn, corn meal, oats, barley, peanuts, wheat and grain flours. These inert ingredients are formulated between 95-100%, individually or as mixtures. Grain ingredients may be mixed with powdered sugar and vegetable or mineral oil, both at 0.1-5%. A rodenticide may be added at the desired concentration either as an individual ingredient or mixed with mineral or vegetable oil or as a pre-mix. Likewise, a dye (another inert ingredient) may be added for the purpose of coloring the diet composition a distinct color (0.1-1%). Dye may be added at the desired concentration either as an individual ingredient or mixed with mineral or vegetable oil or as a pre-mix. Ingredients may be mechanically admixed in commercial mixers and packaged for retail use. Any of the inventive methods, apparatus, or compositions of matter disclosed herein may involve an inert ingredient(s) that forms the non-insecticide, non-rodenticide balance of the diet composition.

Rodent diet compositions may also be formulated using the above-described inert ingredients (e.g., grains, flours) in combination with wax (another inert ingredient). The mix can then be extruded through commercial extruders, which melt the wax dispersed within the mix, followed by cooling the wax to form a bar. Wax concentrations may be between 1-95% and various flours or grains are added between 1-95%. The rodenticide may be added at the desired concentration either as an individual ingredient, or mixed with mineral or vegetable oil, or as a pre-mix. Likewise, a dye may be added for the purpose of coloring the diet composition a distinct color (0.1-1%). The dye may be added at the desired concentration either as an individual ingredient or mixed with mineral or vegetable oil, or as a pre-mix. Rodent diet composition bars (or "bait bars" in colloquial language) may then be packaged for commercial use. Compositions of matter (e.g., diet compositions) that relate to the claimed subject matter may possibly also comprise inert ingredients (e.g., grain, wax, coloring, etc.) as described above or as may be well known in the art.

Diet compositions can also be formulated as gels as referenced in U.S. Pat. No. 6,264,969 (Poché) or as described in other prior art. Examples of rodenticides that are employed for rodent control include, warfarin, diphacinone, chlorophacinone, bromethalin and cholecalciferol, sodium fluoroacetate, coumatetralyl, zinc phospide, brodifacoum, bromodialone, difethialone, difenacoum and flocoumafen. Rodenticide concentrations in the diet may be formulated between 0.001% -0.5%, including, but not limited to the ranges of 0.005% -0.1% and 0.01% -0.05%.

To increase the palatability of diet compositions containing insecticides or to extend the duration of the insecticide action, such chemicals can be microencapsulated. The process may provide a physical barrier between the drug particle and the surrounding environment, shielding the drug from interaction with taste organs or delaying digestion. Microencapsulation technology allows: controlled release of chemicals; enteric release; and taste-masking. Microencapsulation may be carried out by various methods including the use of microcapsules or microparticles that use physical or chemical barriers. Various physical methods of microecapsulation include: spray drying, spray chilling, rotary disk atomization, fluid bed coating, stationary nozzle coextrusion, centrifugal head coextrusion, submerged nozzle coextrusion and pan coating. Chemical methods of encapsulation include: phase separation, solvent extraction, interfacial polymerization, simple and complex coacervation, in-situ polymerization, liposome technology and nanoencapsulation.

Diet compositions can be placed into an uncontrolled setting by: broadcast by manual or mechanical means, spot-baiting by manual or mechanical means, incorporation into a place-pack or blister pack by manual or mechanical means, placement in a reusable or disposable bait station by manual or mechanical means or insertion into rodent burrows by manual or mechanical means.

II. SUMMARY OF THE INVENTION

Certain embodiments of the methods and compositions of matter disclosed herein relate to: "simultaneous" control of rodents and at least one insect pest (e.g., cockroach, ant, tick) using the same bait; control of ticks by orally administering to mammals a diet composition comprising fipronil; enhancing insecticide efficacy through use of a diet composition that comprises a Generation-I rodenticide and an insecticide; use of imidacloprid in a diet composition orally administerable to mammals in an uncontrolled setting; and use of at least one insecticide to enhance the efficacy of a rodenticide. Benefits attendant certain embodiments include but are not necessarily limited to more effect rodent and or insect control, cost and labor savings in achieving a desired control of an insect and/or rodent population.

III. BRIEF DESCRIPTION OF THE DRAWINGS

IV. DETAILED DESCRIPTION OF THE PREFERRED EMBODIMENTS

Figure 1A:
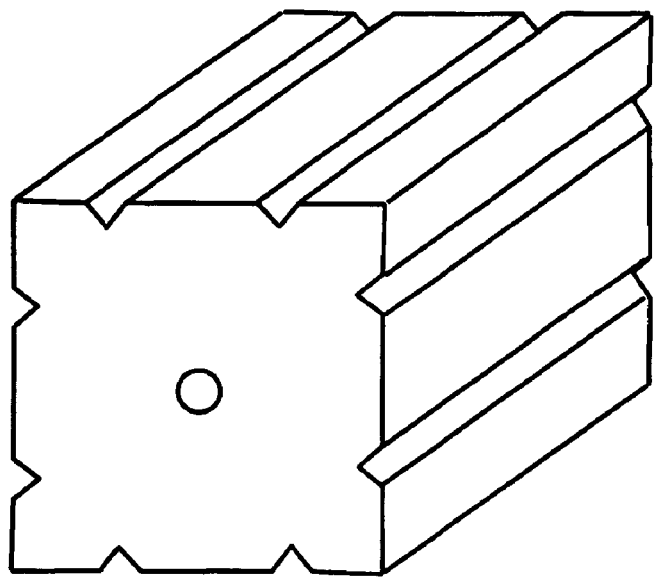
FIG. 1 shows a view of an example of each of three possible forms of diet composition: bar (e.g., extruded wax block), loose grain, and gel.
Figure 1B:
Figure 1C:
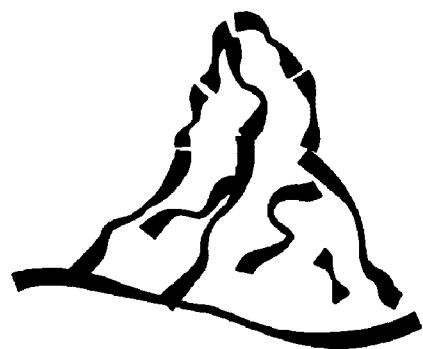
Figure 2:
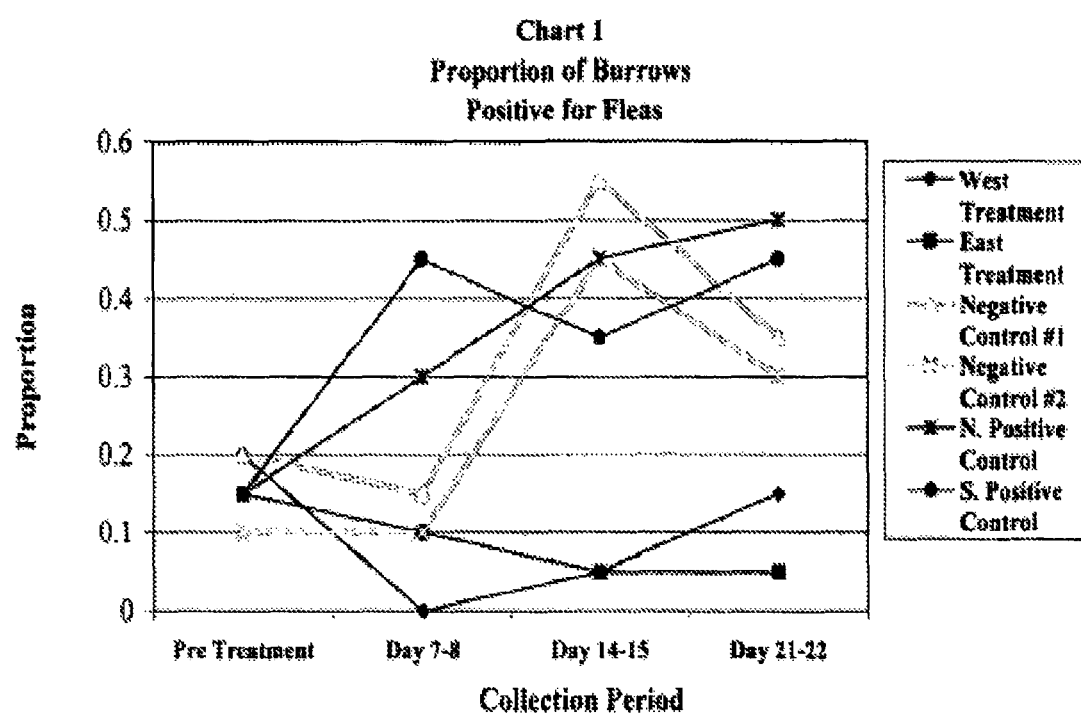
FIG. 2 shows a chart depicting the proportion of burrows positive for fleas over a 22 day period.

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Fipronil Efficacy on Ticks

To investigate the systemic efficacy of fipronil against ticks, diet compositions formulated with the compound were presented to treatment mice while an EPA challenge diet, without insecticide, was presented to control mice. Diet compositions were presented for 48 hours. Water was supplied ad libitum. Feed consumption was monitored throughout the study. After 48-hours, mice were removed from their cages and 50-70 *I. scapularis* were applied to each mouse by first placing mice in 50 ml centrifuge tubes will multiple holes in them. Holes were created by melting the centrifuge tube with a soldering iron. Ticks were then applied and mice remained restrained in the tubes for 2-5 hours, thereby allowing the ticks to attach. The mice were placed in cages suspended over water in a humidity chamber maintaining humidity between 60-80%. Water underneath the suspended mice was checked daily for the presence of ticks falling from the mice. The number of fed and unfed ticks was recorded. Water pans were checked for 6 days. The ticks were kept at 21° C., 90% humidity and a light cycle of 16L:8D. Pans were checked for 5 days. The end-point for the insecticides were larval tick mortality after exposure.

Study 1a: A Diet Composition Containing 970-ppm Fipronil Diet was Formulated Using Inert Ingredients of Rolled Oats, Corn Meal, Powdered Sugar and Corn Oil.

The diet was exposed to laboratory mice for 48 hours.

TABLE 1

Consumption Data of Laboratory Mice Exposed to 970 ppm Fipronil Diet

| Mouse Number | Sex | Presentation Diet composition Weight (g) | Removal Diet composition Weight (g) | Total Diet composition Consumed (g) |
|---|---|---|---|---|
| F3 | M | 138.2 | 137.5 | 0.7 |
| F4 | M | 137.3 | 136.4 | 0.9 |
| F5 | M | 139.1 | 138.1 | 1.0 |
| F6 | M | 136.9 | 135.4 | 1.5 |
| F7 | F | 139.8 | 138.9 | 0.9 |
| F8 | F | 137.2 | 136.3 | 0.9 |
| F9 | F | 139.0 | 134.5 | 4.5 |
| F10 | F | 135.7 | 133.8 | 1.9 |
| | | | Average: | 1.5 |
| C1 | M | 139.1 | 128.8 | 10.3 |
| C2 | F | 142.9 | 136.5 | 6.4 |
| | | | Average: | 8.4 |

TABLE 2

Efficacy of Systemic 970-ppm Fipronil on Larval Ticks (*I. scapularis*) fed on Laboratory Mice

| Mouse Number | Sex | Active Consumed (mg) | Body Weight (kg) | Dose (mg/kg) | Number of Ticks Applied | Replete Ticks |
|---|---|---|---|---|---|---|
| F3 | M | 0.7 | 0.0407 | 17.9 | 50 | 0 |
| F4 | M | 0.9 | 0.0391 | 23.0 | 50 | 0 |
| F5 | M | 1.0 | 0.0379 | 26.4 | 50 | 0 |
| F6 | M | 1.5 | 0.0375 | 40.0 | 50 | 0 |
| F7 | F | 0.9 | 0.0342 | 26.3 | 50 | 0 |
| F8 | F | 0.9 | 0.0354 | 25.4 | 50 | 0 |
| F9 | F | 4.4 | 0.0223 | 197 | 50 | 0 |
| F10 | F | 1.9 | 0.0349 | 54.4 | 50 | 0 |
| | | | | | Total: | 0 |
| C3 | F | NA | 0.0392 | NA | 50 | 0 |
| C4 | M | NA | 0.0327 | NA | 50 | 12 |
| | | | | | Total: | 12 |

Diet compositions containing 960-ppm fipronil were effective at preventing ticks from feeding to repletion on fed mice.
Study 2a: A Diet Composition Containing 485-ppm Fipronil Diet was Formulated and Exposed to Laboratory Mice for 48 Hours.

The diet was exposed to laboratory mice for 48 hours. Ticks were applied directly to the mice. The results are as follows.

TABLE 3

The Efficacy of Systemic Fipronil (485 ppm) on Larval Ticks (*I. scapularis*) Fed on Laboratory Mice

| Mouse Number | Sex | Presentation Diet composition Weight (g) | Removal Diet composition Weight (g) | Total Diet composition Consumed (g) | Number of Ticks Applied | Replete Ticks |
|---|---|---|---|---|---|---|
| 1 | M | 135.0 | 127.1 | 7.9 | 70 | 0 |
| 2 | M | 126.6 | 117.3 | 9.3 | 70 | 0 |

TABLE 3-continued

The Efficacy of Systemic Fipronil (485 ppm) on Larval Ticks
(*I. scapularis*) Fed on Laboratory Mice

| Mouse Number | Sex | Presentation Diet composition Weight (g) | Removal Diet composition Weight (g) | Total Diet composition Consumed (g) | Number of Ticks Applied | Replete Ticks |
|---|---|---|---|---|---|---|
| 3 | M | 129.8 | 118.2 | 11.6 | 70 | 0 |
| 4 | M | 141.8 | 129.8 | 12.0 | 70 | 0 |
| 5 | F | 141.7 | 134.4 | 7.3 | 70 | 0 |
| 6 | F | 131.4 | 116.1 | 15.3 | 70 | 0 |
| 7 | F | 139.1 | 130.8 | 8.3 | 70 | 0 |
| 8 | F | 137.1 | 125.1 | 12.0 | 70 | 0 |
|   |   |   | Average: | 10.4 | Total: | 0 |
| C1 | F | 129.8 | 116.6 | 13.2 | 70 | 41 |
| C2 | F | 129.6 | 114.6 | 15.0 | 70 | 32 |
| C3 | M | 137.8 | 125.2 | 12.6 | 70 | 47 |
| C4 | M | 135.5 | 124.1 | 11.4 | 70 | 42 |
|   |   |   | Average: | 13.1 | Total: | 162 |

These data indicate that diet compositions containing fipronil formulated at 485 mg/kg prevents ticks from feeding to repletion. Fipronil diets may be formulated at 0.001% -1.5% (including the range of 0.01% -0.15%) using diet composition mixing procedures described above. In at least one embodiment of the inventive technology, rodenticides may also be added as part of the composition; such rodenticides include but are not limited to: warfarin, diphacinone, chlorophacinone, bromethalin, sodium fluoroacetate, coumatetralyl, cholecalciferol, zinc phospide, brodifacoum, bromodialone, difethialone, difenacoum and flocoumafen. Rodenticide concentrations in the diet may be formulated from 0.001% -0.5%, including, but not limited to the ranges of 0.005% -0.1% and 0.01% -0.05%. Unless indicated otherwise, all expressed ranges are intended to include their indicated endpoint(s).

Control of Rodents and Cockroaches

Certain aspects of the inventive technology relate to the simultaneous control (e.g., through use of the same diet composition) of ectoparasites and their mammalian hosts and the simultaneous control of rodents/cockroaches and rodents/ants, often in a uncontrolled setting. The term "uncontrolled setting" (e.g., in the "wild" or "field" in colloquial language) is intended as distinguishable from the "controlled" setting characteristic of a research laboratory (e.g. research animals), companion animals (e.g., pets including dogs or cats), a veterinary medicine environment, or a farm animal environment (e.g., horses, sheep, goats or cattle). At least one embodiment of the inventive technology relates to rodents and animals in an uncontrolled setting, a setting that includes both sylvatic areas (affecting only wild animals, including rodents (e.g., prairie dogs, as but one example) away from human habitation) and commensal areas (characterized by a symbiotic relationship in which one species is benefited while the other is unaffected). Generally, commensal refers to rodents, including rats and mice, and other mammals near human habitation.

Cockroaches are a major problem in certain areas of the United States and may contribute to allergies of individuals living in close proximity to them. Cockroaches can potentially transmit disease as well. Cockroaches are know to be very efficient transmitters of disease organisms such as salmonella, dysentery and diarrhea from drains and dumpsters to food surfaces. Cockroaches can carry 32 species of bacteria (including *Salmonella* and *Shigella* species), 15 species of fungi and mold, 7 intestinal parasites, 2 protozoa and 1 virus (Brenner 1995). An additional hazard of cockroaches is long-term infestation. Allergic reaction of to cockroach body parts and feces a recognized as a worldwide public health threat. More that 10 million Americans have experienced allergic reactions to cockroaches. These allergies particularly affect children and can be a predictor in the development of asthma (Miller and Peters 2004)

When attempting to control rodent pests in urban area with conventional technologies, cockroaches often consume this rodent diet composition as well, and the bait includes nothing that is effective against cockroaches. Indeed, rodenticide compounds, which are lethal to rodents, are ineffective against cockroaches. For example, Colvin et al. (1998) indicate that when performing major rodent baiting programs in urban sewers, cockroaches can significantly reduce the amount of rodent bait available to rodents.

Boric acid has been used in cockroach diet compositions for nearly a century. Domestic users can purchase the dust form of the product, which should be applied as a light coating. If the coating is too thick, the insect will simply avoid it. A paste form is available to pest control operators for treatment of cracks and crevices. Boric acid, a stomach action poison, is ingested while the insects clean themselves. Typically applied where the insects are likely to hide, it takes about 10 days to be effective. Boric acid has its shortcomings, however, as it fails to control cockroaches in areas where mold is a problem or where there are large populations of cockroaches. For example, when cockroach diet compositions containing boric acid were placed in sewers, cockroach populations depleted the diet composition before adequate control could be achieved. Diet compositions also became moldy. (Rust et al. 1991).

Numerous other insecticidal compounds to control cockroaches through oral ingestion of insecticides exist including, but not limited to: fipronil, imidacloprid, phenthrin, abamectin, hydropene, hydramethylnon, sulfuramid, eugenol, fenoxycarb, methoprene, propoxur. Many other insecticides or insect growth regulators that could be utilized in such invention are detailed in the Pesticide Action Network Pesticide Database found at www.pesticideinfo.org as appearing on Oct. 24, 2005, in the *Handbook of Pest Control* (Mallis 2004) or *The Pesticide Manual* (Tomlin 2003), each said reference hereby incorporated herein.

Any commercially available insecticides marketed to control cockroaches (e.g., the active ingredients of these products) could be used in particular embodiments of this aspect of the inventive technology. Mixtures of these compounds may be formulated at 0.001% -1.5%, including, but not limited to the ranges of 0.005% -0.1% and 0.01% -0.05%, and rodenticides, using diet composition mixing procedures described above, may be added to effectively control both cockroaches and rodents simultaneously. Rodenticides that may be employed for rodent control include but are not limited to: warfarin, diphacinone, chlorophacinone, Bromethalin, sodium fluoroacetate, coumatetralyl, cholecalciferol, zinc phospide, brodifacoum, bromodialone, difethialone, difenacoum and flocoumafen. Rodenticide concentrations in the diet may be formulated between 0.001% -0.5%, including, but not limited to the ranges of 0.005% -0.1% and 0.01% -0.05%. Attractants to rodent diet compositions containing insecticides and rodenticides could be pheromones, which attract ants or cockroaches to the diet composition for consumption.

This technology could be used in combination with a synergist or potentiator to enhance the efficacy of the poison in controlling the target mammal or insect. Synergists include (but are not limited to) the insecticide synergists: piperonyl butoxide and MGK synergist 264. Potentiators could be in the form of mixtures of insecticides or insect growth regulators, substances that augment the action of each-other. Attractants include but are not limited to pheromones that attract cockroaches to the diet composition. Many other synergists, potentiators or attractants that could be utilized in the inventive technology are detailed in the Pesticide Action Network Pesticide Database found at www.pesticideinfo.org as appearing on Oct. 24, 2005, in the *Handbook of Pest Control* (Mallis 2004) or in *The Pesticide Manual* (Tomlin 2003). Synergists or potentiators could be formulated at 0.1-5%.

To determine if rodent diet compositions containing imidacloprid would be effective at controlling cockroaches, German cockroaches were received from a commercial supplier and placed in a sealed container. Rodent "challenge diet", the EPA standard rodent diet formulation, fortified with 250 mg/kg imidacloprid was placed in the cage. Water was supplied by a wet cotton wick. The mortality of cockroaches consuming diet was 100%.

Using this combination technology, the following cockroach species targeted in this invention include, but are not limited to the following: German Cockroach, *Blattella germanica*; Brownbanded Cockroach, *Supella longipalpis*; Brown Cockroach, *Periplaneta brunnea*; American Cockroach, *Periplaneta americana*; Australian Cockroach, *Periplaneta australasiae*; Smokeybrown Cockroach, *Perilaneta fuliginosa*; Surinam Cockroach, *Pycnoscelus surinamensis*; Oriental Cockroach, *Blatta orientalis*; Asian Cockroach, *Blattella asahina*

Control of Ants and Rodents

Likewise, ants can consume rodent diet composition (e.g., when it is placed in field and urban areas to control rodents). Often, ants infest diet compositions that target rodents and make it unpalatable to rodents. Simultaneous control of ants and rodents would prevent diet composition spoilage due to ants. Possible ants targeted in this invention include, but are not limited to the following: Argentine ant, *Linepithema humile*; Carpenter ant (Pennsylvania), *Camponotus pennsylvanicus*; Carpenter ant (Western), *Camponotus modoc*; Carpenter ant, *Camponotus vicinus*; Crazy ant, *Paratrechina longicornis*; Ghost ant, *Tapinoma melanocephalum*; Odorous house ant, *Tapinoma sessile*; White-footed ant, *Technomyrmex albipes*; Acrobat ant, *Crematogaster* spp.; Bigheaded ant, *Pheidole* spp.; Little Black ant, *Monomorium minimum*; Pavement ant, *Tetrmorium caespitum*; Pharoah ant, *Monomorium pharaonis*; Red Fire ant, *Solenopsis invicta*; Thief ant, *Solenopsis* spp.;

Mixtures of insecticidal compounds may be formulated at 0.001% -1.5% (or, more particularly in some embodiments 0.01% -0.15%, or 0.05% -0.1%) and may be admixed with rodenticides (perhaps using diet composition mixing procedures described above) to effectively control both ants and rodents using the same diet composition. Rodenticides that may be employed for rodent control include, but are not limited to: warfarin, diphacinone, chlorophacinone, bromethalin, sodium fluoroacetate, coumatetralyl, cholecalciferol, zinc phospide, brodifacoum, bromodialone, difethialone, difenacoum and flocoumafen. Rodenticide concentrations in the diet are formulated between 0.001% -0.5%, including, but not limited to the ranges of 0.005% -0.1% and 0.01% -0.05%.

Any of the technologies disclosed here could be used in combination with a synergist or potentiator. Synergists would include but not be limited to the insecticide synergists: piperonyl butoxide and MGK synergist 264. Potentiators could be in the form of mixtures of insecticides or insect growth regulators so as to augment on another's action. Attractants, but are not limited to pheromones that attract ants to the diet composition. Many other synergists, potentiators or attractants that could be utilized in such invention are detailed in the Pesticide Action Network Pesticide Database found at www.pesticideinfo.org as appearing on Oct. 24, 2005, in the *Handbook of Pest Control* (Mallis 2004) or *The Pesticide Manual* (Tomlin 2003). Synergists or potentiators could be formulated at 0.1-5%.

Use of Insecticide and Slow Acting Rodenticide

The anticoagulants warfarin, diphacinone, coumatetralyl, and clorophacinone, are commonly known as the first-generation (generation I) anticoagulants or multiple-feed rodenticides. These compounds are chronic in nature and require rodents to feed on them multiple times, perhaps over several days to a week or more, to kill rodents. In order to achieve this multiple feeding in rodents, diet composition must be made available on a continuous basis until the desired rodent control is obtained. Generation I rodenticides (slow acting rodenticides) are typically formulated from 0.005-0.0500% composition in the bait. These compounds are markedly different than second-generation anticoagulants (generation II), including bromadiolone, difethialone and brodifacoum. These compounds are much more potent than the first-generation anticoagulants. One feeding can produce death if a sufficient amount of diet composition is consumed. These compounds are often referred to as single-feed anticoagulants. Generation II rodenticides are typically formulated between 0.005-0.0500% composition in bait.

Plague caused by *Yersinia pestis* bacteria and other borne diseases including typhus, *Bartonnella* spp., Tungiasis are transferred, in part, by the bite of an infected flea (from the order *Siphonaptera*, including the genus *Xenopsylla, Oropsylla, Tharassis, Ctenocephalides, Echidophaga*). Flea control can substantially decrease the risk of these diseases. It is important to note that when simultaneously controlling rodents and their fleas using systemically delivered insecticides (one mode of simultaneous control involves the use of the same diet composition), it is essential that fleas be controlled first from the insecticide before the rodent host is controlled (e.g., killed) by the rodenticide. Otherwise, as fleas typically only feed on a live mammal host, the fleas will not take a blood meal (or a sufficient number of them) and the insecticide will not enter the insect. Further, a quick kill of the rodent can effect the release of the ectoparasites into the environment, possibly exacerbating the disease transmission problem as they look for new mammal (including human) hosts. Embodiments of this aspect of the inventive technology specifically relate to the use of rodenticides that exhibit a slow-acting effect, thereby allowing sufficient time for insecticides to take effect on ectoparasites. As fleas feed every 3-4 days, to allow adequate insect exposure to systemically delivered insecticides, the rodenticide should not effect a kill of the mammal until after at least 4 days of consumption of the rodenticide (and insecticide, both perhaps part of a diet compositon) by the mammal. Embodiments of this inventive technology (in which a insecticide is used in combination with a slow acting rodenticide) also extend to the simultaneous control of rodents and ectoparasites other than fleas, including *Triatoma* spp., ticks (including the genus *Ixodes* and *Boophilus*), lice and sand flies Slow Acting Rodenticides include but are not necessarily limited to: Warfarin (3-(alpha-acetonylbenzyl)-4-hydroxycoumarin); Chlorophacinone (2-[(p-chlorophenyl)phenylacetyl]-1,3-indandione); Diphacinone (2-diphenylacetyl-1,3-indandione); Coumatetralyl (4-hydroxy-3-(1,2,3,4-tetrahydro-1-naphthyl) coumarin)

These slow acting rodenticides (formulated from perhaps 0.001-0.5%, including, but not limited to the ranges of 0.005% -0.1% and 0.01% -0.05%) could be used in combination with one or more of the following insecticides for flea control: phoxim, cythioate, fipronil, fenoxycarb, ivermectin, proproxur, imidacloprid, dinotefuran and nitenpyram and others. Such insecticides could be formulated at 0.001% -1.5% (including the range of 0.01% -0.15%). Many other insecticides that could be utilized in the inventive technology are detailed in the Pesticide Action Network Pesticide Database found at www.pesticideinfo.org as appearing on Oct. 24, 2005, in the *Handbook of Pest Control* (Mallis 2004) or *The Pesticide Manual* (Tomlin 2003.

This technology could be used in combination with a synergist or potentiator to increase action against fleas either by the metabolism of compounds in the flea or by metabolism of synergistic compounds in rodents. Synergists could include (but are not limited to) the insecticide synergists: piperonyl butoxide, MGK synergist 264 or dimethyl sulfoxide. Many other synergists, potentiators or attractants that could be utilized in such invention are detailed in the Pesticide Action Network Pesticide Database found at www.pesticideinfo.org as appearing on Oct. 24, 2005, in the *Handbook of Pest Control* (Mallis 2004) or *The Pesticide Manual* (Tomlin 2003). Synergists or potentiators could be formulated at 0.1-5%.

For example, an investigation was conducted into the ability of piperonyl butoxide to potentiate the insecticidal activity of orally administered imidacloprid to rats challenged with fleas. Piperonyl butoxide compound is known to produce significant decreases in hepatic cytochrome P450 in rats (Dalvi and Dalvi 1991). Because imidacloprid is also metabolized by cytochrome P450 in rats (Schulz-Jander et al. 2002), decreasing the metabolism rate of imidacloprid in the rat (i.e., the rate at which imidacloprid is metabolized by the rat) may increase the availability and therefore the toxicity of the compound to fleas as well as possibly increasing the residual action of the insecticide. Four rats were evaluated for each test diet. Rats were individually housed in individual cages. Rats were housed in cages measuring 24×40.5×18 cm (L×W×H). The floor area measured 972 cm². Tap water in glass bottles with stainless steel sipper tubes was available ad libitum. Cages were suspended from shelves on two, single-sided racks. Rats were placed in cages identified by a consecutive number 1-8 and a descriptor for their sex (e.g. M or F). PBO Technical (Prentox®) was received from Prentiss Inc. (Floral Park, N.Y., Lot# 41428). Diet composition was made using the following recipes:

TABLE 4

Diet composition Ingredients (g)

| Diet composition | Ground Oats | Corn Meal | Powdered Sugar | Corn Oil | Imidacloprid | PBO |
|---|---|---|---|---|---|---|
| Imi Diet composition | 294.0 | 147.0 | 4.0 | 8.0 | 0.0760 | NA |
| Imi/Pip Diet composition | 294.0 | 147.0 | 4.0 | 4.0 | 0.0767 | 4.0 |

The imidacloprid (Imi) diet composition was formulated at 167 mg/kg imidacloprid. The imidacloprid/PBO diet composition was formulated at 169 mg/kg imidacloprid and 1% PBO. Diets were mixed and presented no-choice to rats for 24 hours. Flea feeding capsules, containing fleas (*X. cheopis*) were secured to the rats and remained attached for 5 hrs. After exposure, the flea feeders were removed and placed in the humidity chamber until the following morning. Fleas were then evaluated for mortality and morbidity (Table 5).

TABLE 5

Efficacy of Imidacloprid and Imidacloprid/Piperonyl Butoxide Diet compositions Against *X. cheopis* Fleas

| Rat Number | Treatment | Sex | Diet Consumed | Average Diet Consumed | # Fleas Dead #Fleas Recovered | Total Percent Mortality (%) |
|---|---|---|---|---|---|---|
| 1 | Imi/pip | M | 18.0 | 19.2 ± 7.6 | 15/15 | 98.6% |
| 2 | Imi/pip | M | 10.9 | | 15/15 | (71/72) |
| 3 | Imi/pip | M | 29.5 | | 16/17 | |
| 4 | Imi/pip | M | 18.3 | | 25/25 | |
| 5 | Imidacloprid | M | 34.1 | 30.5 ± 3.7 | 20/24 | 83.5% |
| 6 | Imidacloprid | M | 25.4 | | 18/18 | (71/85) |
| 7 | Imidacloprid | M | 32.2 | | 15/15 | |
| 8 | Imidacloprid | M | 30.1 | | 18/28 | |

Fleas exposed to rats consuming both imidacloprid and piperonyl butoxide had a higher percent mortality that fleas exposed to rats consuming only imidacloprid diet.

Enhancing the Efficacy of Rodenticides Lethal to Rodents Using Insecticides

Certain insecticides, when used in combination with rodenticides (both slow acting and fast acting) have the potential to increase the efficacy of the rodenticide on the rodent, thereby potentiating its action. For example, both warfarin and imidacloprid (and other insecticides and rodenticides) are metabolized in the rat by cytochrome P450 liver metabolism (Schulz-Jander and Casida 2002, Morin et al. 2004). Other neonicotinoid insecticides metabolized in a similar fashion include acetamiprid, clothianidin, dinotefuran, nitenpyram, thiacloprid, and thiamethoxam. The addition of insecticides to rodenticide diet compositions enables the achievement of the same rodent control effect with a lower percentage concentration of rodenticide because metabolism of the rodenticide may be slowed due to competitive inhibition of insecticide metabolism. Another insecticide metabolized by a cytochrome P450 pathway is the pyrazole insecticide fipronil (Hainzl, 1998). Other pyrazole insecticides include acetoprole, ethiprole, pyrafluprole, pyriprole, tebufenpyrad, tolfenpyrad, vaniliprole; each may be metabolized by a similar pathway.

This rodenticide efficacy enhancement effect could also be described from another perspective: a first diet composition that comprises a rodenticide at a rodenticide concentration, insecticide (e.g., imidacloprid) at a non-zero insecticide concentration (e.g., a non-zero imidacloprid concentration) has a higher rodenticide efficacy (e.g., exhibits a higher rodent mortality) than does a second diet formulation that exhibits the same rodenticide concentration but includes no insecticide (e.g., imidacloprid) whatsoever. It should be noted that the increased efficacy is greater that that increase (presuming one would be observed) that would be observed (as compared with the second diet composition) if the insecticide of the first diet composition were substituted with an equal, additional amount of rodenticide. For purposes of clarity, it is pointed out that: (a) the total concentration of rodenticide in this hypothetical composition would be the numerical value of the rodenticide concentration of the first composition described above plus the numerical value of the insecticide concentration (also of the first composition described above), and (b) that this hypothetical composition comprises no insecticide.

That the addition of an insecticide such as imidicloprid would enhance rodent mortality more that the addition of an equal amount of more rodenticide speaks directly to the unexpected nature of this aspect of the inventive technology and its surprising effect.

As another example: most rodenticide diet compositions for field rodent containing diphacinone are formulated to contain 0.005-0.01% diphacinone; a study involved the combination of 0.0025% diphacinone with 0.025% imidacloprid to evaluate its rodenticide effect on wild rodents (commensal and sylvatic).

Study 1b: A Field Study on Black-Tailed Prairie Dogs in Colorado Using Rodent Diet Composition Formulated at 0.0025% Diphacinone with 0.025% Imidacloprid.

Activity indices were visual count and closed burrow count. EPA guidelines require a 70% reduction in activity. Results of the study are found in Table 6.

TABLE 6

Percent Reduction of Prairie Dogs on Study Plots Treated With Bait Containing 0.0025% Diphacinone with 0.025% Imidacloprid

| Treatment Plot | Index | |
|---|---|---|
| | Visual (%) | Closed Burrow (%) |
| North Treatment[1] | 93.4 | 68.4 |
| South Treatment[1] | 100.0 | 97.3 |

[1]Control data was pooled for each treatment plot and efficacy calculated with the following formula:

$$1 - \frac{\text{Post-Treatment Census Index (Treatment)}}{\text{Pre-Treatment Census Index (Treatment)}} \times \frac{\text{Pre-Treatment Census Index (Control)}}{\text{Post-Treatment Census Index (Control)}} \times 100$$

Study 2b: A Simulated Field Study on Rock Squirrels Using Rodent Diet Composition Formulated at 0.0025% Diphacinone with 0.025% Imidacloprid.

The activity index was observed mortality. Results of the study are found in Table 7.

TABLE 7

Adverse Observations and Efficacy

| Group | # Dead/# Tested | % Efficacy | Adverse Observations |
|---|---|---|---|
| Treatment | 13/18 | 72.2% | HY, H, M, FD |

HY = Hyporeactive,
H = Hemorrhaging,
M = Moribund,
FD = Found Dead

In summary, Diphacinone Rodent Diet Composition (0.0025% Diphacinone) was offered to 18 rock squirrels in a simulated field study. Overall efficacy was 72.2% after 29 days of exposure. This result exceeds the USEPA criterion of 70%.

Study 3b: A Field Study on California Ground Squirrels Using Rodent Diet Composition Formulated at 0.0025% Diphacinone with 0.025% Imidacloprid was Performed.

Activity indices were visual count and closed burrow count. EPA guidelines require a 70% reduction in activity. Results of the study are found in Table 8.

TABLE 8

Efficacy of Diet compositions to Control California Ground Squirrels

| Treatment Plot | Index | |
|---|---|---|
| | Visual | Closed Burrow |
| East Treatment[1] | 85.8% | 74.6% |
| West Treatment[1] | 90.9% | 88.4% |

[1]Control data was pooled for each treatment plot and efficacy calculated with the following formula:

$$1 - \frac{\text{Post-Treatment Census Index (Treatment)}}{\text{Pre-Treatment Census Index (Treatment)}} \times \frac{\text{Pre-Treatment Census Index (Control)}}{\text{Post-Treatment Census Index (Control)}} \times 100$$

Controlling Wildlife Fleas Using Imidacloprid in Uncontrolled Settings

Study 1: Decreasing the Prevalence of Flea Infestation on California Ground Squirrels (*Spermophilus beecheyi*) Using a Rodent Diet Composition Containing 250 ppm Imidacloprid—A Field Trial:

The objective of this study was to determine the effectiveness of grain rodent diet composition containing 250-ppm imidacloprid diet composition for control of fleas on wild ground squirrels (*Spermophilus beecheyi*) in natural field conditions (a type of uncontrolled setting). This study was designed to determine if this product, placed in areas where there is a known population of ground squirrels infested by fleas would decrease the prevalence of flea infestation on the ground squirrels.

Materials and Methods:

Fleas sampling procedures were based on methods described by Davis (1999). The collection of fleas occurred 3 times: once before diet composition was applied (2 days prior to baiting), once after the day 13 baiting and once at the termination of the study (day 29).

Field Rodent Diet Composition (0.025% imidacloprid) was applied at rates of ½ cup (~60 g) per active burrow using measuring cups. Initially, treated diet composition was applied to each burrow on each treatment plot every $3^{rd}$ day (day 0, day 3 and day 6), followed by the same application rate at weekly intervals: at day 13, day 20 and day 27. Diet composition application was designed to bracket the entire life cycle of the target species of fleas. A total of six applications of diet composition were applied: 3 initial and 3 spread one week apart.

Results:

Field Rodent Diet Composition containing imidacloprid (0.025%) significantly decreased the prevalence of flea populations on ground squirrels on the treatment plots. Using the EPA efficacy calculation modified for flea index, the efficacy of Field Rodent Diet Composition for the east and west treatment plots was 93.8% and 100%, respectively at day 15. At day 29, using the EPA efficacy calculation, the efficacy of the east and west treatment plots was 100% and 96.7%

Using the Henderson's efficacy calculation modified by Mount (1976), the efficacy of Field Rodent Diet composition for the east and west treatment plots was 99.4% and 100%, respectively at day 15. At day 29, using the EPA efficacy calculation, the efficacy of the east and west treatment plots was 100% and 100.0%.

On the east control plot, the percentage of squirrels infested with fleas during the pre- and mid-treatment squirrel collection were 88.9% and 100%, respectively. On the west control plot, the percentage of squirrels infested with fleas during the pre- and mid-treatment squirrel collection were 80.0% and 100%, respectively. On the east treatment plot, the percentage of squirrels infested with fleas during the pre- and mid-treatment squirrel collection were 95.7% and 4.5%, respectively. On the west treatment plot, the percentage of squirrels infested with fleas during the pre- and mid-treatment squirrel collection were 95.7% and 0%, respectively.

On the east control plot, the percentage of squirrels infested with fleas during the pre- and post-treatment squirrel collection were 88.9% and 100%, respectively. On the west control plot, the percentage of squirrels infested with fleas during the pre- and post-treatment squirrel collection were 80.0% and 96.3%, respectively. On the east treatment plot, the percentage of squirrels infested with fleas during the pre- and post-treatment squirrel collection were 95.7% and 0%, respectively. On the west treatment plot, the percentage of squirrels infested with fleas during the pre- and post-treatment squirrel collection were 95.7% and 5.0%, respectively.

TABLE 9

Flea Index Data on California Ground Squirrels

| Plot | Pre Treatment Date | Flea Index (Range) | Mid Treatment (Day 15) Date | Flea Index (Range) | Post Treatment (Day 29) Date | Flea Index (Range) |
|---|---|---|---|---|---|---|
| East Control | Jun. 7, 2005 | 5.9 (0-28) | Jun. 24, 2005 | 16.4 (1-47) | Jul. 8, 2005 | 20.5 (1-109) |
| West Control | Jun. 7, 2005 | 7.6 (0-81) | Jun. 24, 2005 | 13.5 (3-43) | Jul. 8, 2005 | 16.4 (0-122) |
| East Treatment | Jun. 7, 2005 | 7.0 (0-39) | Jun. 24, 2005 | 0 (NA) | Jul. 8, 2005 | 0 (NA) |
| West Treatment | Jun. 7, 2005 | 11.0 (0-52) | Jun. 24, 2005 | 0.09 (0-1) | Jul. 8, 2005 | (0.05) (0-1) |

TABLE 10

Percent of California Ground Squirrels Infested with Fleas

| Plot | Pre Treatment Date | Flea Infestation (%) | Mid Treatment (Day 15) Date | Flea Infestation (%) | Post Treatment (Day 29) Date | Flea Infestation (%) |
|---|---|---|---|---|---|---|
| East Control | Jun. 7, 2005 | 88.9 | Jun. 24, 2005 | 100 | Jul. 8, 2005 | 100 |
| West Control | Jun. 7, 2005 | 80.0 | Jun. 24, 2005 | 100 | Jul. 8, 2005 | 96.3 |
| East Treatment | Jun. 7, 2005 | 95.7 | Jun. 24, 2005 | 4.5 | Jul. 8, 2005 | 0 |
| West Treatment | Jun. 7, 2005 | 95.7 | Jun. 24, 2005 | 0 | Jul. 8, 2005 | 5.0 |

TABLE 11

Efficacy of 250 mg/kg Imidacloprid Diet Composition Against the Fleas of California Ground Squirrels Using EPA Method of Calculation

| Plot | Efficacy[1] |
|---|---|
| 15 Day Efficacy | |
| East Treatment | 93.8% |
| West Treatment | 100% |
| 29 Day Efficacy | |
| East Treatment | 100% |
| West Treatment | 96.7% |

[1]Control data was pooled for each treatment plot and efficacy calculated with the following formula:

$$1 - \frac{\text{Post-Treatment Flea Index (Treatment)}}{\text{Pre-Treatment Flea Index (Treatment)}} \times \frac{\text{Pre-Treatment Flea Index (Control)}}{\text{Post-Treatment Flea Index (Control)}} \times 100$$

TABLE 12

Efficacy of 250 mg/kg Imidacloprid Diet Composition Against the Fleas of California Ground Squirrels Using Henderson's Method of Calculation

| Plot | Efficacy[1] |
|---|---|
| 15 Day Efficacy | |
| East Treatment | 99.4% |
| West Treatment | 100% |
| 29 Day Efficacy | |
| East Treatment | 100% |
| West Treatment | 100% |

[1]Control data was pooled for each treatment plot and efficacy calculated with the following formula: $100 - (T/U \times 100)$ T = the post treatment mean divided by the pretreatment mean in the treated site U = the post treatment mean divided by the pretreatment mean in the control site

DISCUSSION AND CONCLUSION

Field Rodent Diet Composition containing imidacloprid (0.025%) was applied 6 times to two field sites in California over a 29 day period. Field Rodent Diet Composition was effective in reducing the on-rodent flea populations of California ground squirrels (*S. beecheyi*) at rates greater than 90% at both day 15 and day 29 in central California.

Study 2c: Field Efficacy of Field Rodent Diet Composition (0.0025% Diphacinone, 0.025% Imidacloprid) in Controlling California Ground Squirrels (*Spermophilus beecheyi*) and their Fleas:

The objective of this study was to determine the effectiveness of grain rodent diet composition containing 25-ppm diphacinone and 250-ppm imidacloprid diet composition for control of wild ground squirrels (*Spermophilus beecheyi*) and their fleas in natural field conditions. The diet composition proposed in this protocol evaluated diphacinone at ½ the typical concentration for controlling ground squirrels. Because the rodenticide active ingredient of this diet composition was formulated at ½ the typical application concentration, less secondary hazards and risks to non-target species were likely. In this study, the efficacy of insecticide/rodenticide diet composition on the control of California ground squirrels was compared to a positive control group that received a commercially available product containing only a rodenticide, and a negative control group (which did not receive bait application).

Materials and Methods:

Six study plots were established:

Two treatment plots evaluating the test substance (diet composition containing 0.0025% diphacinone, imidacloprid 0.025%)

Two negative control plots which received no bait application

Two positive control plots which received a commercially available rodenticide bait containing 0.01% diphacinone, P.C.Q., Bell Laboratories)

Population indices were visual count and closed burrow index. To determine if the formulated diet composition decreased the population of fleas in areas of use, a burrow swabbing technique was performed. Burrow swabbing occurred 4 times during the study:

1. Pre baiting burrow index: On days 3-4 prior to baiting
2. On days 7-8 post first baiting
3. On days 14-15 post first baiting
4. On days 21-22 post first baiting Field Rodent Diet Compostion (0.025% imidacloprid, 0.0025% diphacinone) was applied at rates of ½ cup (~60 g) per active burrow using measuring cups. Initially, a treated diet composition was applied to each burrow on each treatment plot every $3^{rd}$ day (day 0, day 3, day 6 and day 9). P.C.Q. bait was applied to the positive control plots on the same days.

Results:

Field Rodent Diet Composition containing both insecticide and rodenticide was effective at lowering the total number of fleas on treatment plots, the number of fed fleas on study plots and the number of burrows positive for fleas.

TABLE 13

Census Indices of California Ground Squirrels on Study Plots

| | | Index | |
|---|---|---|---|
| Treatment Plot | Study Phase | Visual Count | Closed Burrow |
| East Treatment | Pre-treatment | 12 | 35 |
| | Post-treatment | 1 | 7 |
| West Treatment | Pre-treatment | 19 | 55 |
| | Post-treatment | 1 | 5 |

TABLE 13-continued

Census Indices of California Ground Squirrels on Study Plots

| Treatment Plot | Study Phase | Visual Count | Closed Burrow |
|---|---|---|---|
| Negative Control #1 | Pre-treatment | 31 | 93 |
| | Post-treatment | 21 | 68 |
| Negative Control #2 | Pre-treatment | 34 | 57 |
| | Post-treatment | 17 | 50 |
| North Positive Control | Pre-treatment | 22 | 63 |
| | Post-treatment | 0 | 2 |
| South Positive Control | Pre-treatment | 26 | 66 |
| | Post-treatment | 0 | 4 |

TABLE 14

Efficacy of Baits to Control California Ground Squirrels

| Treatment Plot | Visual | Closed Burrow |
|---|---|---|
| East Treatment[1] | 85.8% | 74.6% |
| West Treatment[1] | 90.9% | 88.4% |
| North Positive Control[1] | 100% | 95.9% |
| South Positive Control[1] | 100% | 92.3% |

[1]Control data was pooled for each treatment plot and efficacy calculated with the following formula:

$$1 - \frac{\text{Post-Treatment Census Index (Treatment)}}{\text{Pre-Treatment Census Index (Treatment)}} \times \frac{\text{Pre-Treatment Census Index (Control)}}{\text{Post-Treatment Census Index (Control)}} \times 100$$

TABLE 15

Number of Fleas Collected From Burrows (n = 20) by Burrow Swab and Plot Flea Index[1]

| Plot | 3-4 Days Before Baiting (Jun. 9, 2005-Jun. 10, 2005) | | Day 7-8 (Jun. 20, 2005-Jun. 21, 2005) | | Day 14-15 (Jun. 27, 2005-Jun. 28, 2005) | | Day 21-22 (Jul. 4, 2005-Jul. 5, 2005) | |
|---|---|---|---|---|---|---|---|---|
| | Number of Fleas | Burrow Index | Number of Fleas | Burrow Index | Number of Fleas | Burrow Index | Number of Fleas | Burrow Index |
| West Treatment | 4 | 0.2 | 0 | 0 | 1 | 0.1 | 15 | 0.8 |
| East Treatment | 7 | 0.4 | 4 | 0.2 | 8 | 0.4 | 18 | 0.9 |
| Negative Control #1 | 5 | 0.3 | 10 | 0.5 | 65 | 3.3 | 19 | 1.0 |
| Negative Control #2 | 2 | 0.1 | 4 | 0.2 | 22 | 1.1 | 13 | 0.7 |
| N. Positive Control | 3 | 0.2 | 20 | 1.0 | 37 | 1.9 | 209 | 10.5 |
| S. Positive Control | 3 | 0.2 | 22 | 1.1 | 366 | 18.3 | 509 | 25.5 |

[1]Plot flea index = Number of fleas collected/number of burrows swabbed (n = 20)

TABLE 16

The Number and Percentage of Burrows (n = 20) Positive for Fleas

| Plot | 3-4 Days Before Baiting (Jun. 9, 2005-Jun. 10, 2005) | | Day 7-8 (Jun. 20, 2005-Jun. 21, 2005) | | Day 14-15 (Jun. 27, 2005-Jun. 28-05) | | Day 21-22 (Jul. 4, 2005-Jul. 5, 2005) | |
|---|---|---|---|---|---|---|---|---|
| | Number of Burrows | % | Number of Burrows | % | Number of Burrows | % | Number of Burrows | % |
| West Treatment | 4 | 20% | 0 | 0% | 1 | 5% | 3 | 15% |
| East Treatment | 3 | 15% | 2 | 10% | 1 | 5% | 1 | 5% |
| Negative Control #1 | 4 | 20% | 3 | 15% | 11 | 55% | 7 | 35% |
| Negative Control #2 | 2 | 10% | 2 | 10% | 9 | 45% | 6 | 30% |
| N. Positive Control | 3 | 15% | 6 | 30% | 9 | 45% | 10 | 50% |
| S. Positive Control | 3 | 15% | 9 | 45% | 7 | 35% | 9 | 45% |

TABLE 17

The Efficacy of Field Rodent Diet Composition Against Burrow Populations of Fleas in California Ground Squirrel Towns Using the EPA Efficacy Formula

| Time Period | West Treatment | | | East Treatment | | |
|---|---|---|---|---|---|---|
| | Total Fleas | Total Fed Fleas | Burrows Positive for Fleas | Total Fleas | Total Fed Fleas | Burrows Positive for Fleas |
| Day 7-8 | 100% | 100% | 100% | 71.5 | 100% | 20.0% |
| Day 14-15 | 98.0% | 93.0% | 92.5% | 90.9 | 87.7% | 90.1% |
| Day 21-22 | 17.5% | 0% | 80.2% | 43.7 | 14.5% | 84.6% |

$$1 - \frac{\text{Post-Treatment Flea Population Index (Treatment)}}{\text{Pre-Treatment Flea Population Index (Treatment)}} \times \frac{\text{Pre-Treatment Flea Population Index (Control)}}{\text{Post-Treatment Flea Population Index (Control)}} \times 100$$

Where a claim as presented herein uses the general term insecticide instead of limiting the subject matter to a specific type of insecticide, the term may potentially include any insecticides from the following list: avermectin insecticides: abamectin, doramectin, emamectin, eprinomectin, ivermectin, selamectin, milbemycin insecticides: lepimectin, milbemectin, milbemycin oxime, moxidectin, benzofuranyl methylcarbamate insecticides: benfuracarb, carbofuran, carbosulfan, decarbofuran, furathiocarb, dimethylcarbamate: insecticides: dimetan, dimetilan, hyquincarb, pirimicarb, oxime carbamate insecticides: alanycarb, aldicarb, aldoxycarb, butocarboxim, butoxycarboxim, methomyl, nitrilacarb, oxamyl, tazimcarb, thiocarboxime, thiodicarb, thiofanox, phenyl methylcarbamate insecticides: allyxycarb, aminocarb, bufencarb, butacarb, carbanolate, cloethocarb, dicresyl, dioxacarb, ethiofencarb, fenethacarb, fenobucarb, isoprocarb, methiocarb, metolcarb, mexacarbate, promacyl, promecarb, propoxur, trimethacarb, xylylcarb, chitin synthesis inhibitors: bistrifluron, buprofezin, chlorfluazuron, cyromazine, diflubenzuron, flucycloxuron, flufenoxuron, hexaflumuron, novaluron, noviflumuron, penfluron teflubenzuron, triflumuron, juvenile hormone mimics: epofenonane, fenoxycarb hydroprene, kinoprene, methoprene, pyriproxyfen, triprene juvenile hormones: juvenile hormone I, juvenile hormone II, juvenile hormone III, moulting hormone agonists: chromafenozide, halofenozide, methoxyfenozide, tebufenozide, moulting hormones: α-ecdysone, ecdysterone, moulting inhibitors: diofenolan, precocenes: precocene I, precocene II, precocene III, unclassified insect growth regulators: dicyclanil, nereistoxin analogue insecticides: bensultap, cartap, thiocyclam, thiosultap, nicotinoid insecticides: flonicamid, acetamiprid, nitroguanidine insecticides: clothianidin, dinotefuran, imidacloprid, thiacloprid, thiamethoxam, nitromethylene insecticides: nitenpyram, nithiazine, pyridylmethylamine insecticides: acetamiprid, imidacloprid, nitenpyram, pyrazole insecticides: acetoprole, ethiprole, pyrafluprole, pyriprole, tebufenpyrad, tolfenpyrad, vanilliprole.

As can be easily understood from the foregoing, the basic concepts of the present invention may be embodied in a variety of ways. It involves both pest control techniques as well as devices to accomplish the appropriate pest control. In this application, the pest control techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this provisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of an "attractant" should be understood to encompass disclosure of the act of "attracting"—whether explicitly discussed or not— and, conversely, were there effectively disclosure of the act of "attracting", such a disclosure should be understood to encompass disclosure of an "attractant" and even a "means for attracting" Such changes and alternative terms are to be understood to be explicitly included in the description.

Any patents, publications, or other references mentioned in this application for patent are hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Provisional patent application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the pest control compositions as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, and xii) each potentially dependent claim or concept as a dependency on each and every one of the independent claims or concepts presented.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

REFERENCES

As with all references mentioned in this application for patent, the following references are hereby incorporated herein by reference.

Colvin, B. A., T. B. Swift, F. E. Fothergill. 1998. Control of Norway Rats in Sewer and Utility Systems Using Pulsed Baiting. In Proc. 18$^{th}$ Vertebr. Pest Conf. R.O. Baker & A.C. Crabb Eds. University of California, Davis.

Brenner, R. J. 1995. Economics and medical importance of cockroaches. Rust, M. K., Owens, J. M., Reiersc, D. A. (editors). *Understanding and Controlling the German Cockroach*: Oxford University Press.

Dalvi, R. R., P. S. Dalvi. 1991. Differences in the effects of piperine and piperonyl butoxide on hepatic drug-metabolizing enzymes systems in rats. Drug Chem Toxicol. 14(1-2): 219-29.

Hainzl D, Cole L M, Casida J E. 1998. Mechanisms for selective toxicity of fipronil insecticide and its sulfone metabolite and desulfinyl photoproduct. Chem Res Toxicol. 1998 December; 11(12):1529-35.

Hedges, S. A. 2004. *Handbook of Pest Control*. Ninth Edition. GIE Media, Inc.

Rust, M. K., Reierson, D. A., Hangen, K. H. 1991. Control of American cockroaches (dictyoptera: Blattidae) in sewers. J. Med Entomology 28(2): 210-213.

Miller, P., B. Peters. 2004. Overview of the public health implications of cockroaches and their management. NSW Public Health Bulletin 15(11-12): 208-211.

Morin S, Bodin L, Loriot M A, Thijssen H H, Robert A, Strabach S, Verstuyft C, Tregouet D A, Dubert L, Laurent-Puig P, Funck-Brentano C, Jaillon P, Beaune P H, Becquemont L. 2004. Pharmacogenetics of acenocoumarol pharmacodynamics. Clin Pharmacol Ther. 2004 May; 75 (5): 403-14.

Shultz-Jander, D. A., W. M. Leimkuelhler, J. E. Casida. 2002. Neonicotinoid insecticides: reduction and cleavage of imidacloprid nitroimine substituent by liver microsomal and cytosolic enzymes. Chem Res Toxicol 15(9): 1158-65.

Shultz-Jander, D. A., J. E. Casida. 2001. Imidacloprid insecticide metabolism: human cytochrome P450 isozymes differ in selectivity for imidazolidine oxidation versus nitroimine reduction. Toxicol Lett. Jun. 7, 2002; 132(1): 65-70.

Tomlin, C. D. S. 2003. *The Pesticide Manual* Thirteenth Edition. British Crop Protection Council, UK.

Hainzl D, Cole L M, Casida J E. 1998. Mechanisms for selective toxicity of fipronil insecticide and its sulfone metabolite and desulfinyl photoproduct. Chem Res Toxicol. December 1998; 11(12):1529-35.

What is claimed is:

1. A method for killing fleas on a mammal comprising the step of orally administering to the mammal in an uncontrolled setting a diet composition comprising imidacloprid and a rodenticide, wherein the composition kills both the mammal and fleas, and wherein the mammal is selected from the group consisting of a rodent, a raccoon, a lagomorph, and a wild canid.

2. The method as described in claim 1 wherein said fleas comprise larvae, subadult fleas, and adult fleas.

3. The method as described in claim 1 wherein said rodenticide is selected from the group consisting of: warfarin, diphacinone, chlorophacinone, bromethalin and cholecalciferol, zinc phospide, sodium fluoroacetate, coumatetralyl, brodifacoum, bromodialone difethialone, difenacoum and flocoumafen.

4. The method as described in claim 1 wherein said diet composition further comprises a synergist or a potentiator.

5. The method as described in claim 1 wherein said uncontrolled setting comprises a sylvatic setting or a commensal setting.

6. The method as described in claim 1 wherein said imidacloprid comprises microencapsulated imidacloprid.

7. The method as described in claim 1 wherein said diet composition further comprises at least one inert ingredient.

* * * * *